US011890119B2

(12) United States Patent
Barnes et al.

(10) Patent No.: US 11,890,119 B2
(45) Date of Patent: *Feb. 6, 2024

(54) TRAY FOR A SOFT TISSUE CUTTING DEVICE AND METHODS OF USE

(71) Applicants: Sonex Health, Inc., Rochester, MN (US); Mayo Foundation for Medical Education and Research, Rochester, MN (US)

(72) Inventors: Darryl E. Barnes, Eagan, MN (US); Aaron Keenan, Austin, MN (US); Jay Smith, Byron, MN (US); Kevin Arnal, Excelsior, MN (US); Sara Schlick, Excelsior, MN (US)

(73) Assignee: Sonex Health, Inc. and Mayo Foundation for Medical Education and Research, Rochester, MN (US)

( * ) Notice: Subject to any disclaimer, the term of this patent is extended or adjusted under 35 U.S.C. 154(b) by 730 days.

This patent is subject to a terminal disclaimer.

(21) Appl. No.: 17/114,022

(22) Filed: Dec. 7, 2020

(65) Prior Publication Data

US 2021/0085417 A1    Mar. 25, 2021

Related U.S. Application Data

(63) Continuation of application No. 15/783,224, filed on Oct. 13, 2017, now Pat. No. 10,864,055.

(51) Int. Cl.
*A61B 50/33* (2016.01)
*A61B 17/3209* (2006.01)
(Continued)

(52) U.S. Cl.
CPC .......... *A61B 50/33* (2016.02); *A61B 17/3209* (2013.01); *A61B 50/20* (2016.02);
(Continued)

(58) Field of Classification Search
CPC ..... A61B 50/33; A61B 17/3209; A61B 50/20; A61B 17/320036; A61B 2017/00557;
(Continued)

(56) References Cited

U.S. PATENT DOCUMENTS

| | | |
|---|---|---|
| 2,123,768 A | 7/1938 | Corsico-Piccolini et al. |
| 3,435,826 A | 4/1969 | Fogarty |

(Continued)

FOREIGN PATENT DOCUMENTS

| | | |
|---|---|---|
| DE | 4444166 A1 | 6/1996 |
| EP | 3193748 A1 | 7/2017 |

(Continued)

OTHER PUBLICATIONS

International Search Report and Written Opinion dated Mar. 25, 2022 in Application No. PCT/US22/70088.

(Continued)

*Primary Examiner* — Shaun L David
*Assistant Examiner* — Rachael L Geiger
(74) *Attorney, Agent, or Firm* — Seager, Tufte & Wickhem LLP (57) ABSTRACT

Methods of using a soft tissue cutting device are disclosed. The methods include providing the soft tissue cutting device, positioning the soft tissue cutting device in a priming slot of a tray configured for receiving and holding the soft tissue cutting device, attaching a priming syringe to the soft tissue cutting device, priming a balloon disposed on a distal end of the soft tissue cutting device by equalizing a first pressure inside the balloon to a second pressure inside the priming syringe, removing the soft tissue cutting device from the priming slot, and positioning the distal end of the soft tissue cutting device on a safety slot included in the tray to determine whether the tissue cutting device has been properly primed.

14 Claims, 8 Drawing Sheets

(51) Int. Cl.
*A61B 50/20* (2016.01)
*A61B 90/00* (2016.01)
*A61B 17/00* (2006.01)
*A61M 25/10* (2013.01)
*A61B 17/32* (2006.01)
*A61B 50/30* (2016.01)
*A61B 50/00* (2016.01)

(52) U.S. Cl.
CPC .............. *A61B 17/320036* (2013.01); *A61B 2017/00557* (2013.01); *A61B 2017/320052* (2013.01); *A61B 2050/005* (2016.02); *A61B 2050/006* (2016.02); *A61B 2050/3008* (2016.02); *A61B 2090/062* (2016.02); *A61M 25/10182* (2013.11)

(58) Field of Classification Search
CPC .. A61B 2017/320052; A61B 2050/005; A61B 2050/006; A61B 2050/3008; A61B 2090/062; A61M 25/10182
See application file for complete search history.

(56) References Cited

U.S. PATENT DOCUMENTS

| | | |
|---|---|---|
| 4,962,770 A | 10/1990 | Agee et al. |
| 4,963,147 A | 10/1990 | Agee et al. |
| 4,979,951 A | 12/1990 | Simpson |
| 5,089,000 A | 2/1992 | Agee et al. |
| 5,125,927 A | 6/1992 | Belanger |
| 5,197,971 A | 3/1993 | Bonutti |
| 5,217,007 A | 6/1993 | Ciaglia |
| 5,306,284 A | 4/1994 | Agee et al. |
| 5,325,883 A | 7/1994 | Orr |
| 5,345,927 A | 9/1994 | Bonutti |
| 5,425,355 A | 6/1995 | Kulick |
| 5,569,283 A | 10/1996 | Green et al. |
| 5,620,446 A | 4/1997 | McNamara et al. |
| 5,649,946 A | 7/1997 | Bramlet |
| 5,655,545 A | 8/1997 | Johnson et al. |
| 5,690,663 A | 11/1997 | Stephens |
| 5,690,664 A | 11/1997 | Sauer et al. |
| 5,702,417 A | 12/1997 | Hermann |
| 5,707,382 A | 1/1998 | Sierocuk et al. |
| 5,709,697 A | 1/1998 | Ratcliff et al. |
| 5,735,865 A | 4/1998 | Schaumann et al. |
| 5,755,732 A | 5/1998 | Green et al. |
| 5,766,198 A | 6/1998 | Li |
| 5,769,865 A | 6/1998 | Kermode et al. |
| 5,769,895 A | 6/1998 | Ripamonti |
| 5,772,680 A | 6/1998 | Kieturakis et al. |
| 5,779,053 A | 7/1998 | Partika et al. |
| 5,782,854 A | 7/1998 | Hermann |
| 5,800,449 A | 9/1998 | Wales |
| 5,810,806 A | 9/1998 | Ritchart et al. |
| 5,813,977 A | 9/1998 | Hinchliffe et al. |
| 5,827,311 A | 10/1998 | Berelsman et al. |
| 5,860,997 A | 1/1999 | Bonutti |
| 5,865,728 A | 2/1999 | Moll et al. |
| 5,893,861 A | 4/1999 | Yumoto |
| 5,904,699 A | 5/1999 | Schwemberger et al. |
| 5,908,433 A | 6/1999 | Eager et al. |
| 5,954,739 A | 9/1999 | Bonutti |
| 5,957,944 A | 9/1999 | Khuri et al. |
| 5,968,061 A | 10/1999 | Mirza |
| 6,004,337 A | 12/1999 | Kieturakis et al. |
| 6,007,554 A | 12/1999 | Van Ess |
| 6,012,586 A | 1/2000 | Misra |
| 6,015,421 A | 1/2000 | Echeverry et al. |
| 6,017,356 A | 1/2000 | Frederick et al. |
| 6,019,774 A | 2/2000 | Weiss et al. |
| 6,030,402 A | 2/2000 | Thompson et al. |
| 6,080,175 A | 6/2000 | Hogendijk |
| 6,083,177 A | 7/2000 | Kobren et al. |
| 6,106,496 A | 8/2000 | Arnissolle |
| 6,113,617 A | 9/2000 | Van Der Merwe |
| 6,117,153 A | 9/2000 | Lary et al. |
| 6,168,608 B1 | 1/2001 | Echeverry et al. |
| 6,171,236 B1 | 1/2001 | Bonutti |
| 6,179,852 B1 | 1/2001 | Strickland et al. |
| 6,217,602 B1 | 4/2001 | Redmon |
| 6,234,996 B1 * | 5/2001 | Bagaoisan ........ A61M 5/31586 604/99.01 |
| 6,258,113 B1 | 7/2001 | Adams et al. |
| 6,264,604 B1 | 7/2001 | Kieturakis et al. |
| 6,346,085 B1 | 2/2002 | Schiffman |
| 6,358,251 B1 | 3/2002 | Mirza |
| 6,361,543 B1 | 3/2002 | Chin et al. |
| 6,402,770 B1 | 6/2002 | Jessen |
| 6,447,529 B2 | 9/2002 | Fogarty et al. |
| 6,451,042 B1 | 9/2002 | Bonutti |
| 6,514,272 B1 | 2/2003 | Kieturakis et al. |
| 6,565,590 B2 | 5/2003 | Kieturakis et al. |
| 6,592,602 B1 | 7/2003 | Peartree et al. |
| 6,632,234 B2 | 10/2003 | Kieturakis et al. |
| 6,685,717 B1 | 2/2004 | Ilic |
| 6,746,465 B2 | 6/2004 | Diederich et al. |
| 6,875,183 B2 | 4/2005 | Cervi |
| 6,896,141 B2 | 5/2005 | McMichael et al. |
| 7,001,405 B2 | 2/2006 | Kieturakis et al. |
| 7,037,317 B2 | 5/2006 | Hermann et al. |
| 7,214,236 B2 | 5/2007 | Kieturakis et al. |
| 7,329,253 B2 | 2/2008 | Brounstein et al. |
| 7,331,462 B2 | 2/2008 | Steppe |
| 7,434,687 B2 | 10/2008 | Itou et al. |
| 7,476,235 B2 | 1/2009 | Diederich et al. |
| 7,481,817 B2 | 1/2009 | Sauer |
| 7,520,886 B2 | 4/2009 | Surti |
| 7,540,875 B2 | 6/2009 | Jessen |
| 7,628,798 B1 | 12/2009 | Welborn |
| 7,708,751 B2 | 5/2010 | Hughes et al. |
| 7,744,617 B2 | 6/2010 | Lunsford et al. |
| 7,780,690 B2 | 8/2010 | Rehnke |
| 7,918,784 B2 | 4/2011 | Wellborn et al. |
| 7,967,137 B2 | 6/2011 | Fulbrook et al. |
| 8,052,710 B2 | 11/2011 | Kambin et al. |
| 8,105,342 B2 | 1/2012 | Onuki et al. |
| 8,147,487 B2 | 4/2012 | Burbank et al. |
| 8,177,064 B2 | 5/2012 | McCormick et al. |
| 8,246,646 B2 | 8/2012 | Kambin et al. |
| 8,252,013 B2 | 8/2012 | Leibowitz et al. |
| D666,725 S | 9/2012 | McCormack et al. |
| 8,257,379 B2 | 9/2012 | Lee |
| 8,273,098 B2 | 9/2012 | Strickland |
| 8,282,665 B2 | 10/2012 | Kieturakis et al. |
| 8,323,278 B2 | 12/2012 | Brecheen et al. |
| D673,683 S | 1/2013 | McCormack et al. |
| D674,489 S | 1/2013 | McCormack et al. |
| 8,348,966 B2 | 1/2013 | McCormack et al. |
| 8,419,728 B2 | 4/2013 | Klotz et al. |
| 8,449,478 B2 | 5/2013 | Lee et al. |
| 8,500,770 B2 | 8/2013 | Echevery et al. |
| 8,523,891 B2 | 9/2013 | Welborn |
| 8,579,930 B2 | 11/2013 | Palmer et al. |
| 8,603,124 B1 | 12/2013 | Hatch |
| 8,603,738 B2 | 12/2013 | Condeelis et al. |
| 8,608,738 B2 | 12/2013 | Brecheen et al. |
| 8,608,763 B1 | 12/2013 | Jurbala |
| 8,613,745 B2 | 12/2013 | Bleich |
| 8,652,157 B2 | 2/2014 | McCormack et al. |
| 8,672,960 B2 | 3/2014 | Briganti et al. |
| 8,702,654 B2 | 4/2014 | Agee et al. |
| 8,721,668 B2 | 5/2014 | McCormack et al. |
| 8,746,452 B2 | 6/2014 | Tomes et al. |
| 8,753,364 B2 | 6/2014 | McCormack et al. |
| 8,876,845 B2 | 11/2014 | Suddaby |
| 8,906,040 B2 | 12/2014 | Filipi et al. |
| 8,911,470 B2 | 12/2014 | Mirza et al. |
| 8,951,273 B1 | 2/2015 | Fard |
| 8,992,424 B2 | 3/2015 | Orbay et al. |
| 9,017,354 B2 | 4/2015 | Fink et al. |
| 9,028,516 B2 | 5/2015 | Palmer et al. |
| 9,050,004 B2 | 6/2015 | Diao et al. |

(56) References Cited

U.S. PATENT DOCUMENTS

| | | |
|---|---|---|
| 9,113,953 B2 | 8/2015 | Smith |
| 9,131,951 B2 | 9/2015 | Mirza et al. |
| 9,168,053 B2 | 10/2015 | Cox |
| 9,168,057 B2 | 10/2015 | Poulsen |
| 9,186,217 B2 | 11/2015 | Goyal |
| 9,532,847 B2 | 1/2017 | Hendrickson et al. |
| 10,206,703 B2 | 2/2019 | Palmer et al. |
| 10,245,062 B2 | 4/2019 | Seymour |
| 10,335,189 B2 | 7/2019 | Aklog et al. |
| 10,357,272 B2 | 7/2019 | Barnes et al. |
| 11,141,186 B2 | 10/2021 | Aklog et al. |
| 11,259,829 B2 | 3/2022 | Barnes et al. |
| 11,259,837 B2 | 3/2022 | Aklog et al. |
| 11,666,356 B2 | 6/2023 | Barnes et al. |
| 2002/0120211 A1 | 8/2002 | Wardle et al. |
| 2002/0161387 A1 | 10/2002 | Blanco |
| 2002/0185406 A1 | 12/2002 | Massengale et al. |
| 2004/0143280 A1 | 7/2004 | Suddaby |
| 2004/0195131 A1 | 10/2004 | Spolidoro |
| 2005/0209624 A1 | 9/2005 | Vijay |
| 2005/0222598 A1 | 10/2005 | Ho et al. |
| 2005/0228426 A1 | 10/2005 | Campbell |
| 2006/0149136 A1 | 7/2006 | Seto et al. |
| 2006/0190021 A1 | 8/2006 | Hausman et al. |
| 2007/0083225 A1 | 4/2007 | Kiser et al. |
| 2007/0112366 A1 | 5/2007 | Welborn et al. |
| 2007/0118170 A1 | 5/2007 | Kieturakis et al. |
| 2007/0225740 A1 | 9/2007 | Suddaby |
| 2008/0033466 A1 | 2/2008 | Assell et al. |
| 2008/0058588 A1 | 3/2008 | Emanuel |
| 2008/0058846 A1 | 3/2008 | Vosough |
| 2008/0109021 A1 | 5/2008 | Medoff |
| 2008/0195128 A1 | 8/2008 | Orbay et al. |
| 2008/0234713 A1 | 9/2008 | Bernardini |
| 2008/0288041 A1 | 11/2008 | Holman et al. |
| 2009/0048620 A1 | 2/2009 | Weiss et al. |
| 2009/0048623 A1 | 2/2009 | Afosse et al. |
| 2009/0125044 A1 | 5/2009 | Lary |
| 2009/0171157 A1 | 7/2009 | Diederich et al. |
| 2009/0312740 A1 | 12/2009 | Kim et al. |
| 2009/0312807 A1 | 12/2009 | Boudreault et al. |
| 2010/0010530 A1 | 1/2010 | Rhee |
| 2010/0100114 A1 | 4/2010 | Berger |
| 2010/0125266 A1 | 5/2010 | Deem et al. |
| 2010/0185222 A1 | 7/2010 | Keller |
| 2010/0211082 A1 | 8/2010 | Sauer |
| 2010/0249719 A1 | 9/2010 | Fojtik |
| 2010/0311026 A1* | 12/2010 | Tomes ............... A61M 25/002 434/262 |
| 2011/0087258 A1 | 4/2011 | Sluss |
| 2011/0112563 A1 | 5/2011 | To et al. |
| 2011/0118601 A1 | 5/2011 | Barnes et al. |
| 2011/0155599 A1 | 6/2011 | Yakel et al. |
| 2011/0201881 A1 | 8/2011 | Emch |
| 2012/0016398 A1 | 1/2012 | Strickland |
| 2012/0029542 A1 | 2/2012 | Huang |
| 2012/0029543 A1 | 2/2012 | Lee |
| 2012/0191116 A1 | 7/2012 | Flynn et al. |
| 2012/0198703 A1 | 8/2012 | Ranieri et al. |
| 2012/0203220 A1 | 8/2012 | Brannan et al. |
| 2012/0289987 A1 | 11/2012 | Wilson et al. |
| 2012/0303018 A1 | 11/2012 | Ladtkow et al. |
| 2013/0046323 A1 | 2/2013 | Whitaker |
| 2013/0066149 A1 | 3/2013 | Mirza et al. |
| 2013/0144318 A1 | 6/2013 | Dinis Carmo |
| 2013/0165962 A1 | 6/2013 | Porshinsky et al. |
| 2013/0172895 A1 | 7/2013 | Wallace et al. |
| 2013/0197553 A1 | 8/2013 | Ng et al. |
| 2013/0211201 A1 | 8/2013 | Wongsiri |
| 2013/0289596 A1 | 10/2013 | Guo |
| 2013/0345515 A1 | 12/2013 | Fitzmaurice |
| 2014/0012076 A1 | 1/2014 | Mirza et al. |
| 2014/0031621 A1 | 1/2014 | Liu |
| 2014/0039533 A1 | 2/2014 | Palmer et al. |
| 2014/0054356 A1 | 2/2014 | Hartwick et al. |
| 2014/0066709 A1 | 3/2014 | Mirza et al. |
| 2014/0121456 A1 | 5/2014 | McCormack et al. |
| 2014/0180282 A1 | 6/2014 | Brecheen et al. |
| 2014/0276741 A1 | 9/2014 | McKay |
| 2014/0276790 A1 | 9/2014 | Raybin et al. |
| 2014/0343357 A1 | 11/2014 | Mirza et al. |
| 2014/0371526 A1 | 12/2014 | Mirza et al. |
| 2015/0045822 A1 | 2/2015 | Mirza et al. |
| 2015/0073461 A1 | 3/2015 | McCormack et al. |
| 2015/0080878 A1 | 3/2015 | Feng et al. |
| 2015/0080905 A1 | 3/2015 | Begemann et al. |
| 2015/0133982 A1 | 5/2015 | Park |
| 2015/0182248 A1 | 7/2015 | Palmer et al. |
| 2015/0196743 A1 | 7/2015 | Diederich et al. |
| 2015/0201959 A1 | 7/2015 | Guo |
| 2015/0265818 A1 | 9/2015 | Piskun et al. |
| 2015/0282832 A1 | 10/2015 | Mirza et al. |
| 2015/0320436 A1 | 11/2015 | Agee et al. |
| 2016/0038172 A1 | 2/2016 | Cox |
| 2016/0081710 A1* | 3/2016 | Barnes ............ A61B 17/320036 606/170 |
| 2016/0157880 A1 | 6/2016 | Aklog et al. |
| 2016/0235431 A1 | 8/2016 | Brown et al. |
| 2017/0042565 A1 | 2/2017 | Ellsworth et al. |
| 2017/0086803 A1 | 3/2017 | Nakanishi et al. |
| 2017/0105792 A1 | 4/2017 | Barnes et al. |
| 2017/0325797 A1 | 11/2017 | Ladtkow et al. |
| 2018/0338774 A1 | 11/2018 | Pajardi et al. |
| 2019/0262024 A1 | 8/2019 | Barnes et al. |
| 2021/0085417 A1 | 3/2021 | Barnes et al. |
| 2022/0218383 A1 | 7/2022 | Barnes |
| 2022/0233232 A1 | 7/2022 | Barnes et al. |

FOREIGN PATENT DOCUMENTS

| | | |
|---|---|---|
| EP | 3278749 A1 | 2/2018 |
| EP | 3766440 A1 | 1/2021 |
| EP | 3908215 A1 | 11/2021 |
| EP | 3975889 A1 | 4/2022 |
| WO | 2007016141 A2 | 2/2007 |
| WO | 2013155472 A1 | 10/2013 |
| WO | 2014118752 A2 | 8/2014 |
| WO | 2014176206 A2 | 10/2014 |
| WO | 2014176206 A3 | 1/2015 |
| WO | 201831617 A1 | 12/2018 |
| WO | 2020247476 A1 | 12/2020 |
| WO | 2022150837 A1 | 7/2022 |
| WO | 2022232582 A1 | 11/2022 |

OTHER PUBLICATIONS

International Search Report and Written Opinion dated Sep. 21, 2020, in International Application No. PCT/US20/35094.
Extended European Search Report for Application No. 20738258.1 dated Feb. 23, 2022.
International Search Report and Written Opinion dated Jun. 15, 2020, in Application No. PCT/US20/12682.
Trigger Tome® Minimally Invasive Trigger Finger Release System, 1 page, www.sonicsurg.com 2023. Accessed Jun. 26, 2023.
Hebbard et al., "Ultrasound-Guided Microinvasive Carpal Tunnel Release using a Novel Retractable Needle-Mounted Blade: A Cadaveric Study," Journal of Ultasound Medicine, vol. 37, No. 8, pp. 2075-2081, Aug. 2018.
MicroAire Upper Extremity Carpal Tunnel, https://www.microaire.com 2 pages. Accessed Jun. 26, 2023.
MICROi™BLADE—A Micro Invasive Surgical Instrument, 10 pages. www.microi-tool.com.Accessed Jun. 26, 2023.
Muramatsu et al., "A Comparison of Blinded Versus Ultrasound-Guided Limited-Open Trigger Finger Release using the Yasunaga Knife," Journal of Hand Surgery, Asian Pacific, vol. 27, No. 1 pp. 124-129, Feb. 2022.
S2S Surgical™ Surgeon-2-Surgeon Innovation, The Future of Minimally Invasive Hand Surgery, 3 pages, 2023.
Summit Medical, About Innovia Medical, 1 page, https://summitmedicalusa.com/ 2023. Accessed Jun. 26, 2023.

(56) References Cited

OTHER PUBLICATIONS

Invitation To Pay Additional Fees dated Mar. 31, 2023 for International Application No. PCT/US2023/011838.
U.S. Appl. No. 15/783,224, filed Oct. 13, 2017, Tray for a Soft Tissue Cutting Device and Methods of Use.
U.S. Appl. No. 17/113,996, filed Dec. 7, 2020, Tray for a Soft Tissue Cutting Device and Methods of Use.
U.S. Appl. No. 62/086,950, filed Dec. 3, 2014 (52 pages).
Search Report and Written Opinion dated Feb. 15, 2016, issued in International Application No. PCT/US2015/049558 (24 pages).
Examination Report issued in European Patent Application No. 15767038.1, dated Apr. 29, 2019 (8 pages).
Information about Related Patents and Patent Applications, see section 6 of the accompanying Information Disclosure Statement Letter, which concerns Related Patents and Patent Applications.

\* cited by examiner

TRAY FOR A SOFT TISSUE CUTTING DEVICE AND METHODS OF USE

RELATED APPLICATIONS AND CLAIM OF PRIORITY

This patent document claims priority to, and is a continuation of, U.S. patent application Ser. No. 15/783,224 filed Oct. 12, 2017. The disclosure of the priority patent application is fully incorporated into this document by reference.

TECHNICAL FIELD

The present disclosure generally relates to a tray for a soft tissue cutting device, and more particularly to a tray for storage, priming, and set up of a soft tissue cutting device used for treatment of carpal tunnel syndrome.

BACKGROUND

Carpal tunnel syndrome affects approximately 3.7% of the general population and up to 7% of manual labor workers. Several varying surgical procedures are performed annually to treat patients with carpal tunnel syndrome. One of these surgical procedures is known as a carpal tunnel release procedure ("CTR procedure"). During the CTR procedure a transverse carpal ligament is cut in order to reduce median nerve compression and carpal tunnel pressures in the carpal tunnel region.

An example of a device used in a CTR procedure is described in the commonly-assigned U.S. application Ser. No. 14/854,775, titled "Soft Tissue Cutting Device and Methods of Use." The device includes a blade having a top cutting edge that can be moved forward and backwards. The device also includes one or more balloons that can be inflatable. The balloons can expand radially so as to create and/or expand the "safe zone," the narrow space between the median nerve and the ulnar artery in the carpal tunnel in which the transverse carpal tunnel ligament can be cut without risk to the median nerve or ulnar artery. As the radially expanding balloons inflate, they move the flexor tendons, median nerve, and ulnar neurovascular bundle away from the device to help create a region in which the transverse carpal ligament can be cut while preventing nearby at-risk structures from being cut.

SUMMARY

In general, this disclosure relates to a method of using a soft tissue cutting device. In various implementations, the methods may include providing the soft tissue cutting device, positioning the soft tissue cutting device in a priming slot of a tray configured for receiving and holding the soft tissue cutting device, attaching a priming syringe to the soft tissue cutting device, priming a balloon disposed on a distal end of the soft tissue cutting device by equalizing a first pressure inside the balloon to a second pressure inside the priming syringe, removing the soft tissue cutting device from the priming slot, and positioning the distal end of the soft tissue cutting device on a safety slot included in the tray to determine whether the tissue cutting device has been properly primed.

In some implementations, attaching the priming syringe may include attaching a priming syringe that include a plunger housed within and movable relative to a syringe body. In such implementations, priming the balloon may include fluidly connecting the priming syringe to the soft the tissue cutting device, depressing the plunger of the priming syringe a first time to deliver fluid into the balloon to fill the balloon with the fluid, and drawing back the plunger a first time to create a vacuum and deflate the balloon. Optionally, priming the balloon may also include depressing the plunger of the priming syringe a second time to refill the balloon with the fluid, drawing the plunger back a second time to create a vacuum and thereby deflate the balloon, depressing the plunger a third time, and allowing the pressure within the balloon to equalize with the pressure in the priming syringe.

In certain implementations, providing the soft tissue cutting device comprises providing a soft tissue cutting device that includes a balloon activation lever that is movable between a depressed position and an extended position and positioned on a proximal end opposite to the distal end. When the tissue cutting device is positioned in the priming slot for priming, the balloon activation lever is in an intermediate position between the depressed position and the extended position. In such implementations, the methods may also include moving the balloon activation lever from the intermediate position to the extended position when the tissue cutting device is removed from the priming slot after priming. Optionally, the methods may include:

Inserting the soft tissue cutting device into a soft tissue of a subject when the balloon activation lever is in the extended position, moving the balloon activation lever to the depressed position, and deploying a blade working end of a blade to cut the soft tissue. Moving the balloon activation lever to the depressed position may cause the balloon to expand outwardly from the blade. A slider button may be moved to cause the blade working end to protrude out of a housing shaft of the soft tissue cutting device such that the blade working end is deployed to cut the soft tissue. Optionally, the slider button can only be moved after expansion of the balloon. The methods may also include releasing the balloon activation lever from the depressed position to deflate the balloon, and pulling the soft tissue cutting device from the subject. Moving the balloon activation lever from the intermediate position to the extended position may cause the balloon to deflate. Additionally and/or alternatively, the methods may include depressing the balloon activation lever to the depressed position to inflate the balloon after removing the tissue cutting device from the priming slot prior to positioning the tissue cutting device on the safety slot to determine whether the tissue cutting device has been properly primed.

In some implementations, the safety slot may have a safety slot width configured to be narrower than a distal end width of a distal end of the soft tissue cutting device when the soft tissue cutting device is properly primed for use. As such, when the distal end of the soft tissue cutting device does not fall through the safety slot, the soft tissue device is determined to be properly primed.

The methods may also include providing the tray including the priming slot and the safety slot. Optionally, attaching the priming syringe to the soft tissue cutting device may include positioning the priming syringe in a priming syringe slot included in the tray.

The details of one or more examples are set forth in the accompanying drawings and the description below. Other features, objects, and advantages will be apparent from the description and drawings, and from the claims.

BRIEF DESCRIPTION OF DRAWINGS

The following drawings are illustrative of particular embodiments of the present disclosure and therefore do not limit the scope of the invention. The drawings are not necessarily to scale (unless so stated) and are intended for use in conjunction with the explanations in the following detailed description. Embodiments of the present disclosure will hereinafter be described in conjunction with the appended drawings, wherein like numerals denote like elements.

DETAILED DESCRIPTION

The following detailed description is exemplary in nature and is not intended to limit the scope, applicability, or configuration of the disclosure in any way. Rather, the following description provides some practical illustrations for implementing examples of the present disclosure. Examples of constructions, materials, dimensions, and manufacturing processes are provided for selected elements, and all other elements employ that which is known to those of ordinary skill in the field of the disclosure. Those skilled in the art will recognize that many of the noted examples have a variety of suitable alternatives.

Certain embodiments of the present disclosure provide a tray for a device, such as a soft tissue cutting device. While the illustrated embodiments show an exemplary embodiment of a soft tissue cutting device, such as a transverse carpal ligament cutting device, it should be understood that many different types of devices can be shipped, primed and tested prior to use according to systems and methods disclosed herein.

Figure 1:
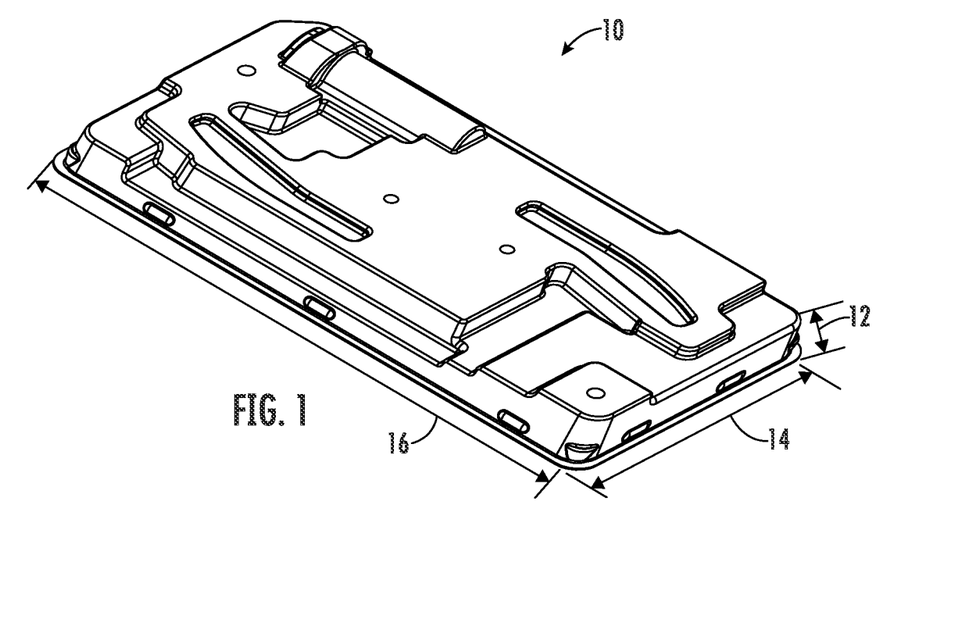
FIG. 1 is an upper perspective view of a tray with a device according to a non-limiting exemplary embodiment.
Figure 2:
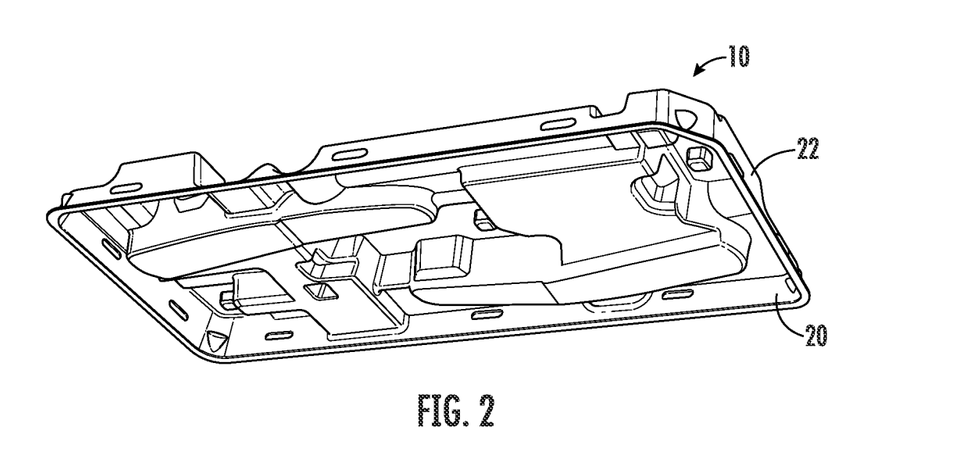
FIG. 2 is a lower perspective view of FIG. 1.

FIGS. 1 and 2 are upper and lower perspective views of a tray 10 for enclosing a device 100 (not shown) according to an exemplary embodiment. Tray 10 has a tray thickness 12, a tray width 14, and a tray length 16. Tray 10 includes a body 20 and a cover 22.

The tray 10 can be made by molding polymers such as resins or copolyesters. In one embodiment, the tray 10 is made by molding polyethylene terephthalate-glycol (PET-G). Other materials are within the scope of the present disclosure. In addition, in certain embodiments, the tray 10 may be shipped in a sealed bag (not shown) so as to ensure that the tray 10 and the device (e.g., device 100) housed therein are sterile.

In some embodiments, the tray 10 has generally rounded corners and may not have sharp edges. Advantageously, this may promote ease of use during surgery. For instance, the rounded edges and corners of the tray 10 prevent catching on and/or tearing of surgical gloves worn by medical personnel when grasping and/or manipulating the tray 10. In the illustrated embodiment, the tray 10 is generally rectangular in shape, with a tray thickness 12 less than tray width 14 and tray length 16, though other shapes are contemplated within the scope of the present disclosure.

In certain exemplary embodiments, the tray length 16 is between about 10 inches and about 20 inches. Further, in some embodiments, the tray width 14 is between about 5 inches and about 10 inches, and the tray thickness 12 is between about 0.5 inch and 3 inches. In an exemplary embodiment, the tray length 16 is about 16 inches, the tray width 14 is about 7.5 inches and the tray thickness 12 is about 1.33 inches. It should be noted, however, that these dimensions are not limiting.

Figure 3:
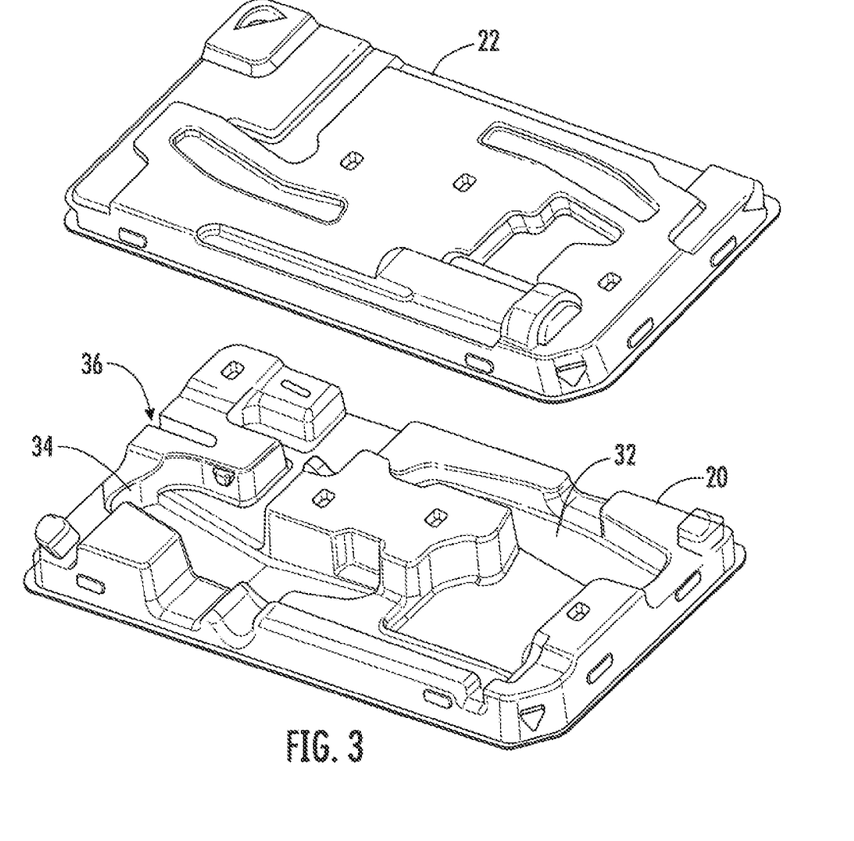
FIG. 3 is an exploded perspective view of the tray of FIG. 1 shown without a device.

FIG. 3 is an exploded perspective view of the tray 10 according to an exemplary embodiment. The tray 10 includes a body 20, a cover 22, and a plurality of slots 32, 34, and 36. The cover 22 can be removably connectable to the body 20. When the cover 22 is connected to the body 20 of the tray 10, the cover 22 substantially encloses the body 20 and its contents. In certain advantageous embodiments, the cover 22 can be a sterile cover, and may not be removed except when the tray 10 is in use for a procedure, such as a CTR procedure.

Figure 4:
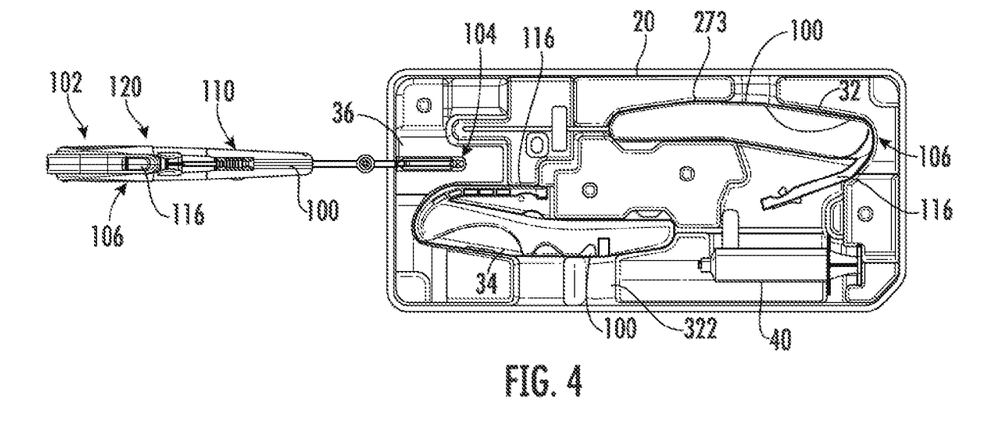
FIG. 4 is a top view of the tray of FIG. 1 showing various positions of a device with the tray.

FIG. 4 is a perspective view of the tray 10 with a device 100 shown in various positions within the tray 10. The tray includes a body 20 and a plurality of slots 32, 34, 36. Each of the slots 32, 34, and 36 of the tray 10 receive and/or are connected to the device 100 to illustrate various positions of the device 100 when housed in different slots 32, 34, 36 of the tray 10. It should be understood that in certain embodiments, the tray 10 is shipped with a single device 100 housed in the slot 32 and a priming syringe 40 as will be described further below.

In certain embodiments, the device 100 as illustrated in FIG. 4 can be a soft tissue cutting device 100, such as described in the commonly-assigned application Ser. No. 14/854,775 ("the '775 application"), the entire contents of which is hereby incorporated by reference. It should be noted however, that the present disclosure is not limited to the disclosed embodiment of device 100 in the '775 application and many variants thereof are contemplated within the scope of the present disclosure.

With continued reference to FIG. 4, the device 100, according to an embodiment, can be a soft tissue cutting device, such as a transverse carpal ligament cutting device. The device 100 has a proximal end 102 and a distal end 104. The proximal end 102 includes a handle 106 and a balloon activation lever 116. The handle 106 includes a blade activation assembly 110. The device 100 also includes an inflation assembly 120 coupled to the handle 106. The inflation assembly 120 and blade activation assembly 110 each control various functions of the shaft at the distal end 104.

Figure 5:
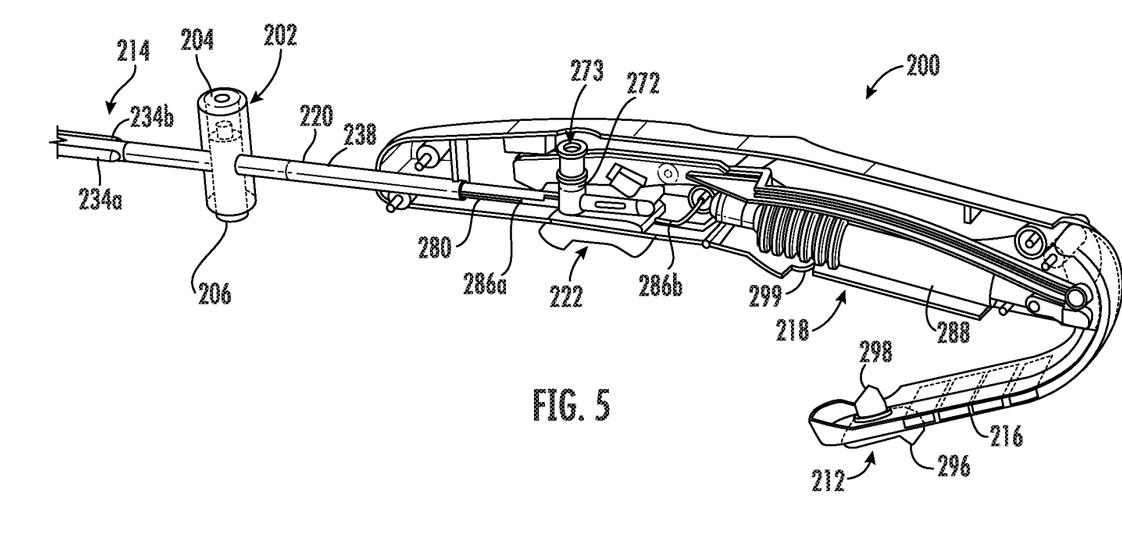
FIG. 5 is a perspective view of a soft tissue cutting device with its outer housing removed to illustrate interior detail.
Figure 6:
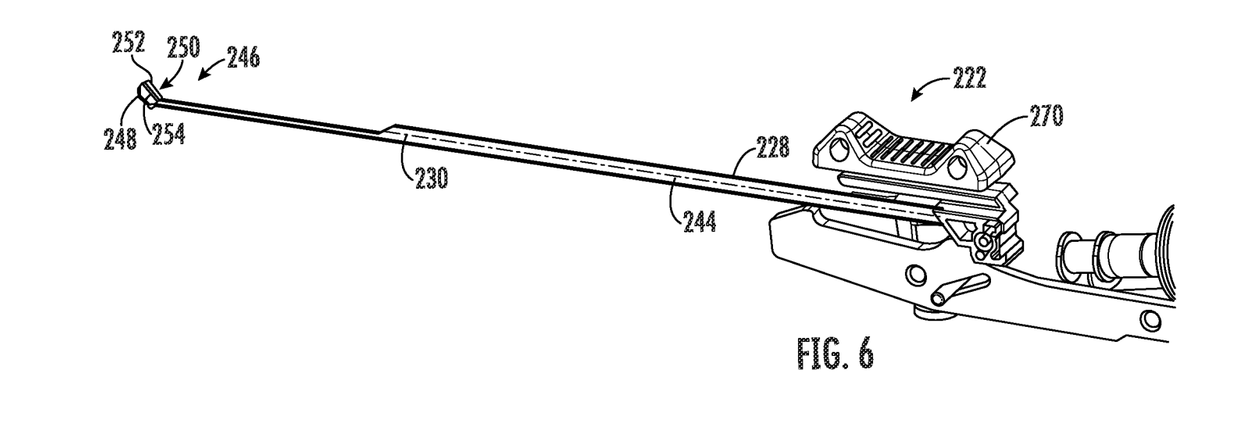
FIG. 6 is partial perspective view of a blade and blade activation assembly of the soft tissue cutting device shown in FIG. 5.
Figure 7:
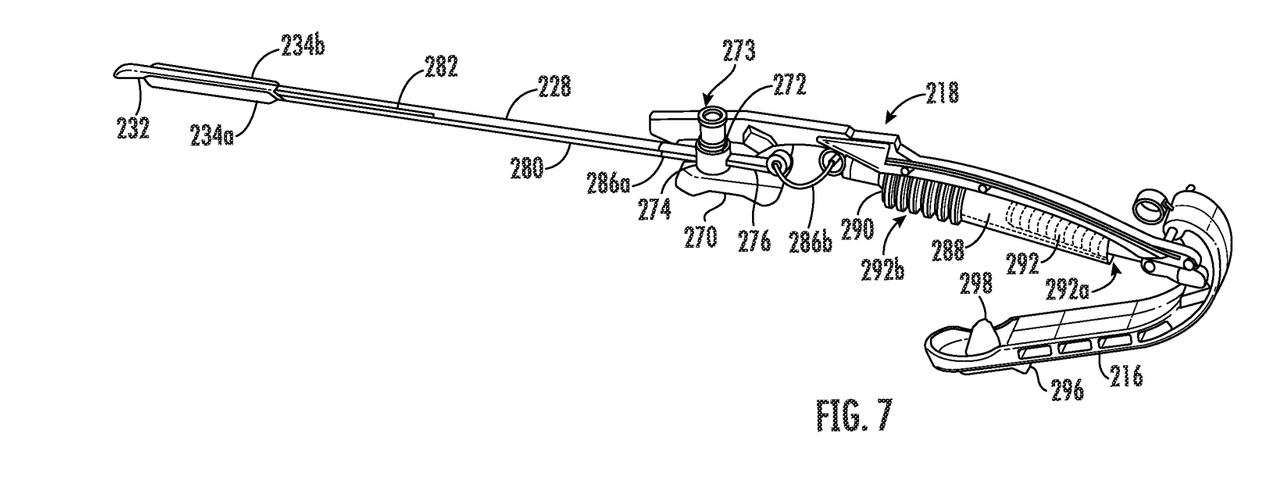
FIG. 7 is a perspective view of the device shown in FIG. 5 with its outer housing removed to illustrate interior detail.

FIGS. 5, 6 and 7 are perspective views of a soft tissue cutting device 200 according to an embodiment of this disclosure. FIG. 5 is a perspective view of the soft tissue cutting device 200 with its outer housing removed to illustrate interior detail. FIG. 6 is partial perspective view of a blade activation assembly 222 and a blade 228 of the soft tissue cutting device 200 shown in FIG. 5. FIG. 7 is a perspective view of the device 200 shown in FIG. 5 with its outer housing removed to illustrate interior detail.

The device 200 can be substantially similar to device 100. The device 200 has a proximal end 212 and distal end 214. The proximal end 212 includes a balloon activation lever 216 (similar to the balloon activation lever 116 of device 100). The distal end 214 includes an axial depth indicator 202 with ends 204 and 206. The axial depth indicator is located on a shaft 220 that has a top surface 238. A blade 228 is housed at least partially within the shaft 220. A pair of balloons 234a and 234b is located on shaft 220. Device 200 also includes an inflation assembly 218 and a blade activation assembly 222.

The shaft 220 of device 200 can have a tip that is smooth edged (e.g., rounded) to permit ease of insertion into the carpal tunnel region. The shaft 220 can optionally be echogenic and/or include diagnostic equipment to permit visualization of the carpal tunnel region during insertion or surgery. The axial depth indicator 202 can be a spring-loaded pin that is slidable along the shaft 220 by pressing ends 204 and 206 toward each other. The axial depth indicator 202 can thus be used to indicate the depth of insertion of the distal end 214 into the patient.

The balloons 234a and 234b expand radially outwardly from the shaft 220. When inflated, the balloons 234a, 234b have a spherical, oval, bilobular or other configuration. When deflated, the balloons 234a, 234b are generally flush with the shaft 220. The balloons 234a and 234b can be positioned anywhere along the shaft 220 such that they, for example, expand (or create) the safe zone in a patient's carpal tunnel region. While two lateral balloons 234a, 234b are illustrated, skilled artisans will understand that any number of radially expanding balloons can be used and be placed anywhere about the shaft 220 to secure the distal end 214 in position within the carpal tunnel region and to expand the safe zone. For instance, in an exemplary embodiment, as the radially expanding balloons 234a, 234b inflate, they move the flexor tendons, median nerve, and ulnar neurovascular bundle away from the device 200 to help create a region in which the transverse carpal ligament can be cut while preventing nearby at-risk structures from being cut, effectively increasing the "safe zone."

The balloons 234a, 234b can have any desired configuration that allows them to inflate and deflate. In some embodiments, the entire balloon is expandable and thus inflates and deflates. In other embodiments, only part of the balloon is expandable. For example, the balloon can have a fixed portion and an expandable portion. The balloons 234a, 234b also inflate to a desired size selected to accommodate the size of a patient's wrist (and thus the patient's carpal tunnel region). For example, in some cases, the balloons 234a, 234b can be provided with a specific size such that when they are fully inflated, they have a specific inflated size. In one embodiment, each of the balloons 234a, 234b inflate to a similar or same diameter (e.g., a diameter of about 1.5 mm). In patients with larger wrists, larger balloons can be used. In patients with smaller wrists, smaller balloons can be used. In another embodiment one of the balloons 234a, 234b inflates to one size and another inflates to a different size. In other cases, the balloons 234a, 234b can have a standard size but can be partially inflated or fully inflated to have a variety of different inflated sizes. In some cases, the balloon inflation can be graded to allow the operator to choose a particular balloon diameter. In certain cases, the balloon inflation can be pressure dependent, such that the balloon manually or automatically inflates until a specific pressure is exerted on the balloon surface.

The blade activation assembly 222 actuates the blade 228 through a slot 232 located on distal end 214. In the illustrated example, the slot 232 is positioned near (and between) the balloons 234a, 234b, though, of course, the slot 232 may be positioned at other locations in the distal end 214. The blade activation assembly 222 is coupled to a blade shaft 244. The blade 228 includes a blade working end 246. The blade shaft 244 has a longitudinal axis 230 along which the blade 228 is actuated. In the illustrated embodiment, the blade working end 246 is configured as a hook and configured to cut a transverse carpal ligament. The blade working end 246 includes an inner surface 250 that adjoins an outer surface 248 at a point 252. The blade working end 246 also includes a cutting edge 254. In some embodiments, the cutting edge 254 can be non-parallel to the blade shaft 244. Alternatively, the cutting edge 254 can be non-linear (e.g., curved). The blade shaft 244 engages with the blade activation assembly 222 to move the blade 228 forward (distally) and backward (toward the proximal end 212) in a direction parallel to the longitudinal axis 230.

In some embodiments, instead of including a cutting edge 254, at least part of the entire outer surface 248 (or substantially the entire outer surface 248 or the entire outer surface 248) can be a dull and/or blunt surface that would not cut body tissue. Likewise, the point 252 may be a dull and/or blunt surface. Additionally, a limiting stop can be positioned near the blade working end 246 to engage with and/or travel within a guided surface (e.g., a groove, guide, track or tunnel) that guides the forward and rearward movement of the blade 228. Such embodiments are advantageous, as they assist in cutting the target tissue in a controlled fashion, while preventing inadvertent cutting of tissue other than the target tissue.

The blade activation assembly 222 includes a slider button 270 positioned on an external surface of the balloon activation lever 216. The slider button 270 can move in both forward and backward directions (parallel to the longitudinal axis 230) to move the blade 228 forward and backward. An operator can engage the slider button 270 with a finger (for example by engaging a thumb with the slider button 270). When the slider button 270 is moved to extend the blade 228, the blade working end 246 protrudes through the slot 232 in the distal end 214.

The inflation assembly 218 includes a fluid coupling 272 and a fill port 273. In the embodiment shown, the fluid coupling 272 is T-shaped and includes a first port 274 and a second port 276 and is connected to the fill port 273. The inflation assembly 218 also includes a first tube 280, a second tube 282, a first conduit 286a, a second conduit 286b, and an inflation device 288.

The fluid coupling 272 is coupled to the fill port 273. The first port 274 is fluidly coupled to (e.g., by fluid fittings such as push-fit or barbed fitting) a first conduit 286a. The second port 276 is fluidly coupled to a second conduit 286b (e.g., by fluid fittings such as push-fit or barbed fitting). The first conduit 286a is fluidly coupled to the first tube 280 and the second tube 282. The first tube 280 is fluidly coupled to the first balloon 234a, and the second tube 282 is fluidly coupled to the second balloon 234b. Accordingly, when the fill port 273 engages with a priming device (e.g., priming syringe) that supplies pressurized fluid (e.g., by a plunger), the fluid travels through the fluid coupling 272, into the first conduit 286a (via the first port 274), through the first tube 280 and the second tube 282 and into the first balloon 234a and the second balloon 234b to inflate and pressurize the balloons.

The second conduit 286b is fluidly coupled to the inflation device 288. In the embodiment shown, the inflation device 288 is located inside of the balloon activation lever 216, though in other embodiments, the inflation device 288 can be located outside of the balloon activation lever 216. Skilled artisans will also understand that the inflation assembly 218 described in this embodiment can also be included in any of the other device embodiments (e.g., device 100) described herein. In the embodiment shown, the inflation device 288 is a bellows that includes a body 290 and a spring-biased plunger 292 with a distal end 292a and a proximal end 292b. The body 290 is shown as a transparent feature to illustrate interior detail. The spring-biased plunger 292 is pivotally coupled to the balloon activation lever 216. When the balloon activation lever 216 is depressed, the plunger 292 moves towards distal end 292a. When the balloon activation lever 216 is released, the spring-bias of the plunger 292 moves the plunger 292 toward proximal end 292b.

In other embodiments, the inflation device 288 can be in the form of a syringe with a piston or plunger or the like. Alternatively, the inflation device 288 can be any desired device known in the art that holds inflation material and both pushes inflation material out of the inflation device 288 and pulls inflation material back into the inflation device 288. The inflation device 288 is actuated by the balloon activation lever 216 to inflate or deflate the balloons 234a, 234b once primed.

When the balloons 234a, 234b are deflated, the fluid from the balloons 234a, 234b travel to and stay within the bellows 288. In order to re-inflate the balloons 234a, 234b, the balloon activation lever 216 is engaged, thereby applying pressure on the distal end 292a of the plunger 292 of the bellows 288 to pressurize fluid within the bellows 288. This causes fluid to move into the first conduit 286a, through the first tube 280 and the second tube 282, and into the balloons 234a, 234b. When the operator desires to deflate the balloons 234a, 234b, the balloon activation lever 216 is released. The plunger 292 of the bellows 288 then moves toward the proximal end 292b as a result of spring bias, thereby pulling fluid back towards the inflation device 288. As a result, the fluid moves out of the balloons 234a, 234b and back into first tube 280 and second tube 282, through the first conduit 286a, and into the bellows 288.

The balloon activation lever 216 includes a balloon locking mechanism. In the embodiment shown, the balloon locking mechanism includes a spring-biased button 296, which terminates in a pin 298. The device 200 includes a groove 299 for receiving the pin 298 of the button 296. If the operator desires to lock the balloons 234a, 234b in an inflated position, the balloon activation lever 216 is depressed to bring the spring-biased button 296 toward the groove 299 (e.g., by an operator's thumb or finger). The pin 298 of the spring-biased button 296 is then received within the groove 299. When the pin 298 rests within the groove 299, the plunger 292 of the inflation assembly 218 is held in tension against its spring-bias, thereby maintaining the position of the balloon activation lever 216 in the depressed position and the plunger 292 near the proximal end 292b of the bellows 288. As a result, the fluid would continue to be pressurized, thereby maintaining the balloons 234a, 234b in an inflated position.

Prior to use, the device 200 is in a first inactive position. In the first inactive position, the blade 228 positioned such that the cutting edge 254 is fully housed and protected within the shaft 220 and the device 200 can be safely inserted into a carpal tunnel region. Additionally, the balloons 234a, 234b are in a deflated configuration. The operator inserts the distal end 214 of the device 200 into a carpal tunnel region such that the transverse carpal ligament is positioned adjacent the top surface 238 of the shaft 220. The operator then engages the balloon activation lever 216 to cause the balloons 234a, 234b inflate and expand the safe zone within the carpal tunnel region. The balloons 234a, 234b can then be locked in the inflated state using the balloon locking mechanism to engage the spring-biased button 296 to maintain the pin 298 in the groove 299.

The operator next moves the slider button 270 to move the blade working end 246 to protrude out of the shaft 220, and fully expose the cutting edge 254 to cut the transverse carpal ligament. The operator continues to move the slider button 270 to move the blade working end 246 (and cutting edge 254) in a desired direction (e.g., backward). As the cutting edge 254 moves along the desired direction (e.g., backward), it cuts the transverse carpal ligament. Once the transverse carpal ligament is cut, the operator releases the spring-biased button 296 and the balloon activation lever 216. As a result of the spring-bias, the plunger 292 moves toward distal end 292a. As a result, the balloons 234a, 234b deflate. In this second position, the blade 228 is positioned such that the blade working end 246 does not protrude out of the shaft 220, the cutting edge 254 is fully housed and protected within the shaft 220, and the device 200 can thus be safely removed from the body.

Figure 8:
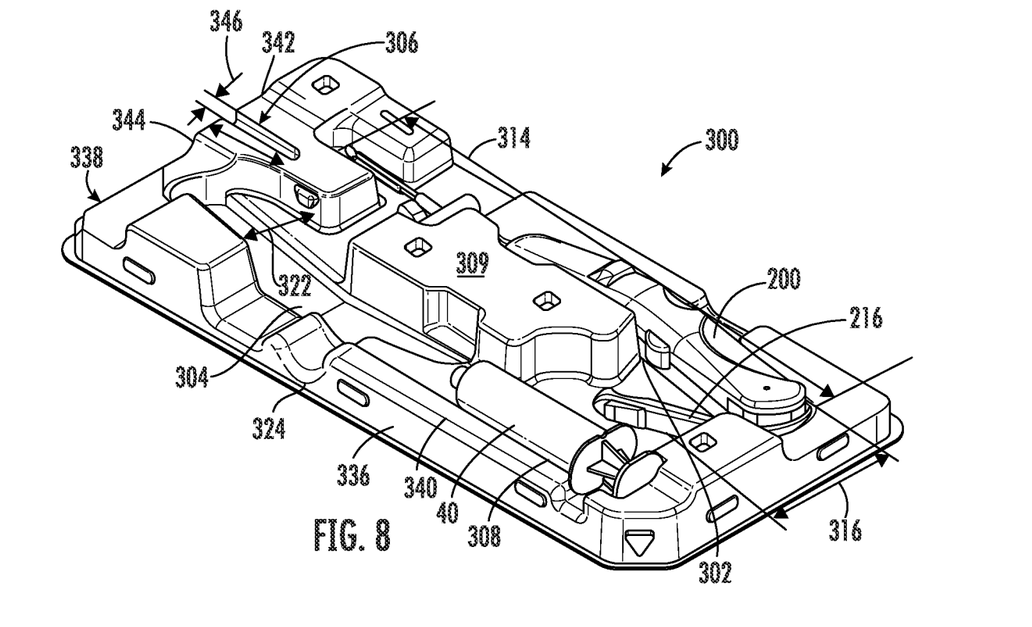
FIG. 8 is a side perspective view of the tray of FIG. 1 with the device housed in the housing slot.
Figure 9:
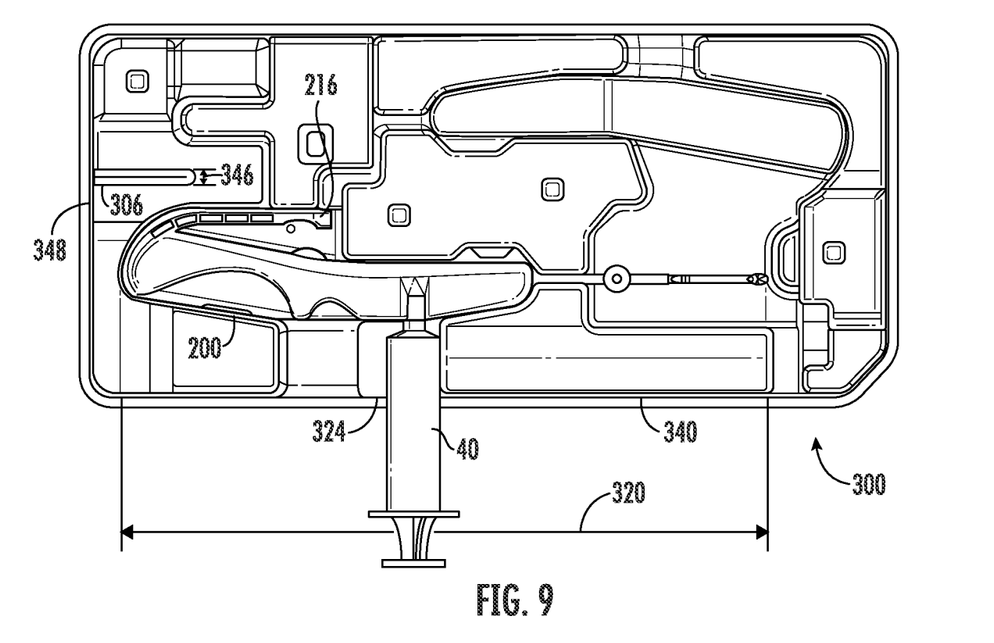
FIG. 9 is a top view of the tray of FIG. 1 with the device housed in the priming slot.
Figure 10:
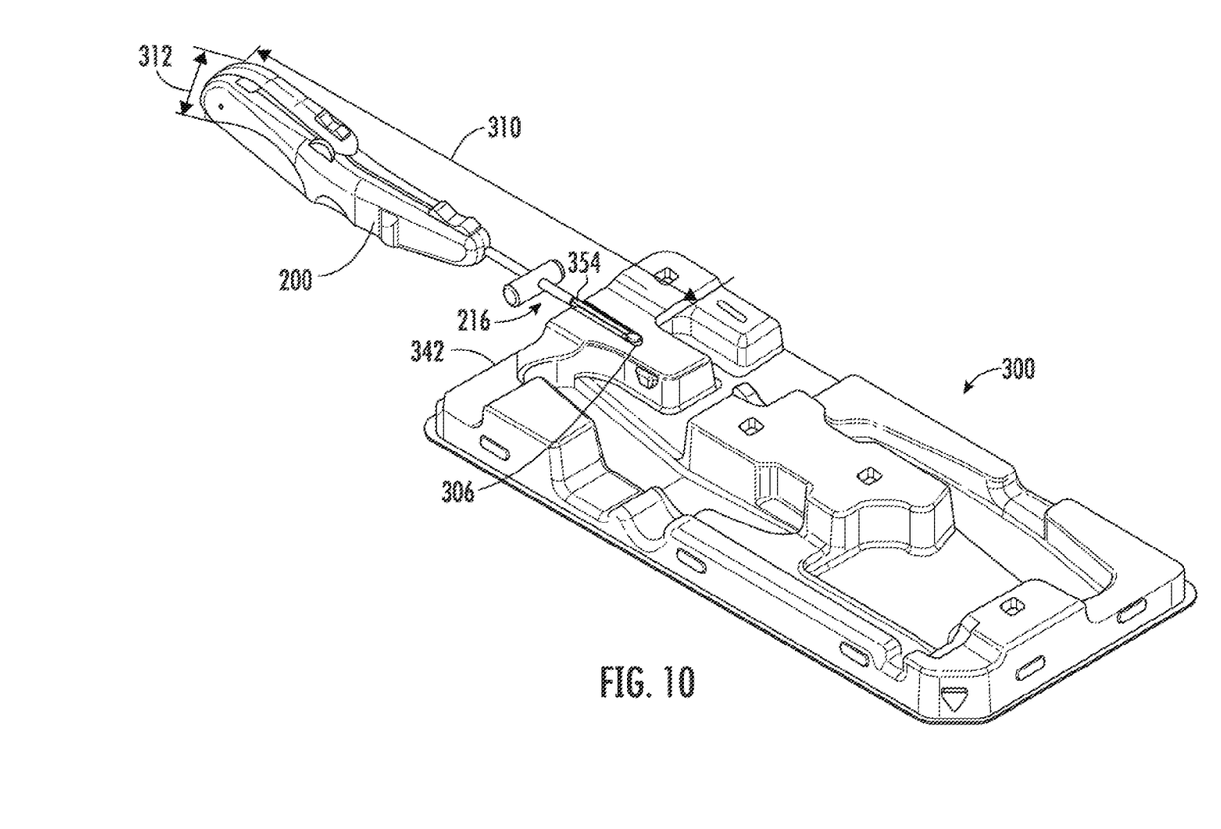
FIG. 10 is an upper perspective view of the tray of FIG. 1 with the device near the safety slot when the priming has been correctly performed.
Figure 11:
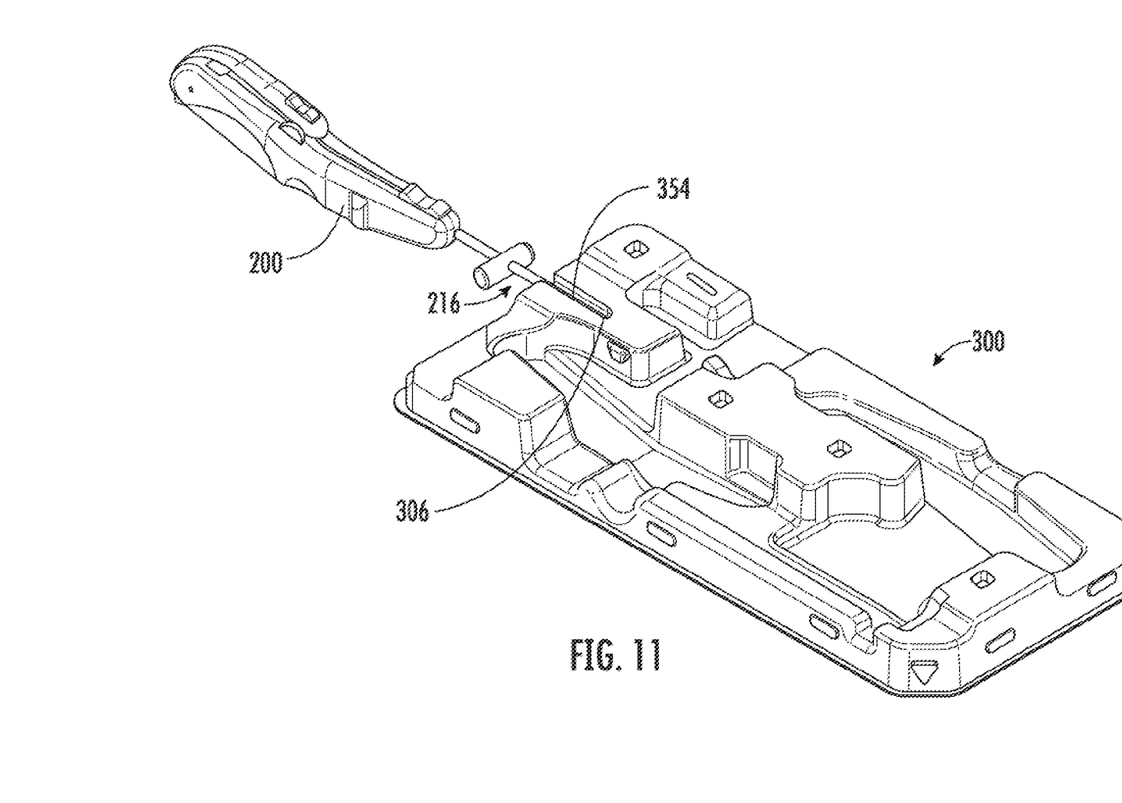
FIG. 11 is an upper perspective view of the tray of FIG. 1 with the device received in the safety slot when the priming has been incorrectly performed.

FIG. 8 is a side perspective view of a tray 300 with the device 200 in a housing slot 302 and the priming syringe 40 in a priming syringe slot 308. FIG. 9 is a top view of the tray 300 with the device 200 housed in a priming slot 304. FIG. 10 is an upper perspective view of the tray 300 with the device 200 resting on safety slot 306 when priming of the device 200 has been correctly performed. FIG. 11 is an upper perspective view of the tray 300 with the device 200 received in the safety slot 306 when priming of the device 200 has not been correctly performed.

Referring to FIGS. 8-11, the tray 300 includes the housing slot 302, the priming slot 304, the safety slot 306, the priming syringe slot 308, and a top surface 309. The device 200 has a device length 310 and a device width 312. The housing slot 302 has a housing slot length 314 and a housing slot width 316. The priming slot 304 has a priming slot length 320 and a priming slot width 322. A lateral groove 324 is adjacent to the priming slot 304. The tray 300 also includes a first side surface 336 and a second side surface 338, both of which are perpendicular to the top surface 309. A first edge 340 adjoins the top surface 309 and the first side surface 336. A second edge 342 adjoins the top surface 309 and the second side surface 338. The safety slot 306 has a safety slot length 344 and a safety slot width 346.

As shown in FIG. 8, the priming syringe 40 can be supplied along with the device 200 and housed in the tray 300 in the form of a surgical kit. During shipment and prior to use, the device 200 can be removably housed in the housing slot 302. Further, the priming syringe 40 can be removably housed in the priming syringe slot 308. The housing slot 302 is elongated in shape. As shown in FIG. 8, the elongated shape of the housing slot 302 generally matches the elongated shape of the device 200. The housing slot 302 is a cavity recessed from the top surface 309 of the tray 300. The priming syringe slot 308 is also a cavity recessed from the top surface 309 and is shaped to match the shape of the priming syringe 40.

The housing slot 302 can be shaped to match the shape of the device 200 prior to priming to receive the device 30 in a snug fashion. For instance, the housing slot width 316 can be equal to (or slightly greater than) the device width 312 and the housing slot length 314 can be equal to (or slightly greater than) the device length 310. The housing slot 302 is shaped such that the balloon activation lever 216 of the device 200 is in an extended (or released) position. The priming slot 304 is recessed from the top surface 309 and can be shaped to generally match the shape of the device 200 during a priming procedure. The priming slot length 320 can be about equal to the housing slot length 314. In some embodiments, the priming slot width 322 can be slightly less than the housing slot width 316, because, as discussed below, during priming, the balloon activation lever 216 is in a position different from its position when in the housing slot 302.

The safety slot 306 is located on the second edge 342 adjoining the top surface 309 and the second side surface 338. The safety slot 306 is recessed from the top surface 309 and is generally elongated in shape. The safety slot length 344 is generally shorter than the housing slot length 314 and/or the priming slot length 320. Further, in some embodiments, the safety slot width 346 can be narrower than both the housing slot width 316 and the priming slot width 322.

As shown in FIG. 9, once the device 200 is ready for priming, the device 200 can be removed from the housing slot 302, and the priming syringe 40 can be removed from the priming syringe slot 308 and placed laterally near the fill port 273. Once removed, the device 200 can be positioned and aligned with the lateral groove 324 so as to facilitate connection to the priming syringe 40. The lateral groove 324 is defined on the first side surface 336 near the first edge 340. As shown in FIG. 9, during priming, a portion of the priming syringe 40 is positioned and held within the lateral groove 324, such that the distal tip of the priming syringe 40 can engage with the fill port 273 of the device 200 positioned in the priming slot 304. When the device 200 is positioned in the priming slot 304, the balloon activation lever 216 is in an intermediate position between the depressed position and the extended position. The balloon activation lever 216 is movable to the depressed position to inflate the balloons after priming, and to the extended position to deflate the balloons after priming.

In order to prime the device 200 prior to use, in certain exemplary embodiments, the priming syringe 40 is used. In one example, priming involves filling the balloons with a fluid and initially pressurizing the balloons prior to use. For example, the priming syringe 40 can have a plunger which is used to dispense a fluid through the distal tip into a fluid conduit and thereby into the balloons of the device 200. The plunger can be movable with respect to the body of the priming syringe 40. Other types of priming devices (e.g., injectors, pumps, and the like) are also contemplated within the scope of the present disclosure.

In some embodiments, the priming syringe 40 can be removably connectable with the fill port on the device 200. For instance, the removable connection between the fill port and the priming syringe 40 can be a Luer-Lok® connection. The fill port in turn can be fluidly connected to the balloons by way of conduits. Thus, the priming syringe 40 can be fluidly coupled to the balloons such that movement of the plunger of the priming syringe 40 can create a vacuum and/or deflate the balloons, or fill the balloons with a predetermined volume of fluid and/or inflate the balloons. In one embodiment, when the plunger of the priming syringe 40 is drawn, a vacuum is created within the balloons. When the plunger of the priming syringe 40 is depressed, the balloons may be filled with a predetermined volume of fluid. Further, the balloons can be deflated and re-inflated successively to equalize balloon pressure to the pressure within the syringe, as will be described further below.

In an exemplary embodiment, the priming syringe 40 contains about 20 milliliters of saline, and pressurizes the balloons by providing between about 1 milliliter and about 2 milliliter of saline. However, the volumes provided herein should not be construed as limiting. Further, fluids other than saline can also be used to prime the balloons.

Figure 12:
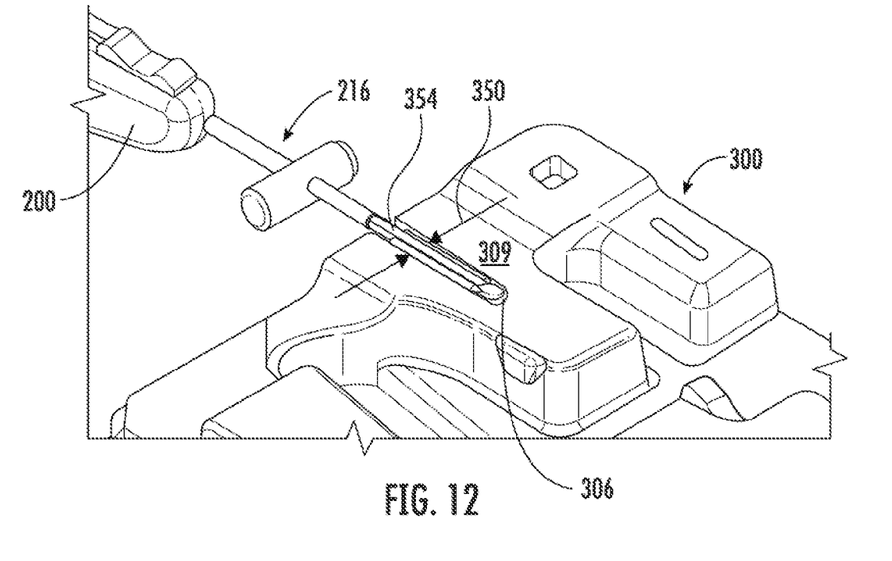
FIG. 12 is an enlarged perspective view of the safety slot of FIG. 10.
Figure 13:
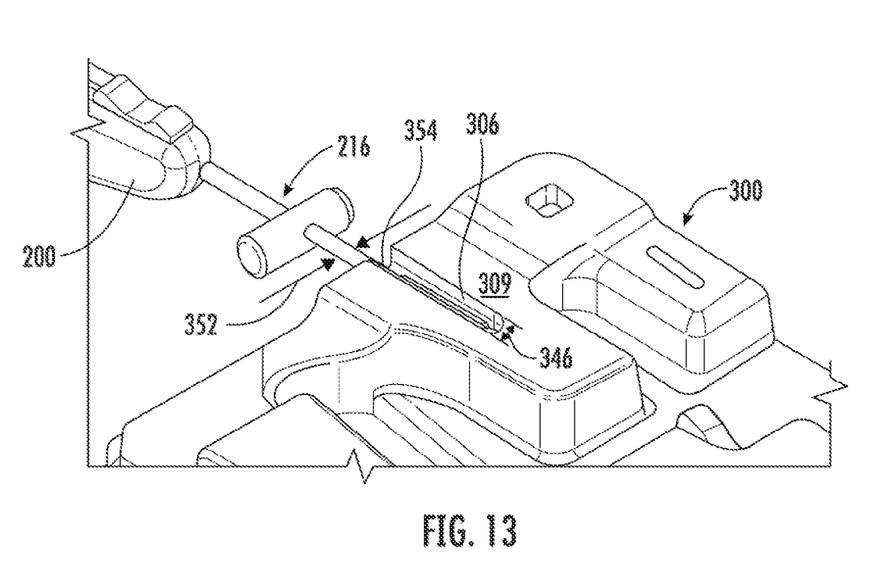
FIG. 13 is an enlarged perspective view of the safety slot of FIG. 12.

After the device 200 has been primed, the safety slot 306 is used to determine whether the device 200 is primed such that it is ready for use. FIGS. 10-13 illustrate a test for determining whether the balloons have been properly primed for use. FIG. 12 is an enlarged perspective view of the device 200 in safety slot 306 as shown in FIG. 10. FIG. 13 is an enlarged perspective view of the device 200 in safety slot 306 as shown in FIG. 11.

FIGS. 10 and 12 show the device 200 in the safety slot 306 when the device 200 is properly primed. When the device 200 is properly primed, the balloons are inflated such that the distal end of the device 200 has a first distal end width 350. When the device 200 is properly primed, the first distal end width 350 is larger than the safety slot width 346 such that the distal end of the device 200 does not fall into the safety slot 306 and instead rests on top of the safety slot 306. Furthermore, a top portion 354 of the distal end extends above the top surface 309 of the tray 300. This indicates that the balloons are sufficiently inflated for use and thus that the device 200 has been properly primed.

FIGS. 11 and 13 show the device 200 in the safety slot 306 when the device 200 is not properly primed. When the device 200 has not been properly primed, the balloons are underinflated such that the distal end of the device has a second distal end width 352 that is narrower than the first distal end width 350. When the balloons have not been properly primed, the second distal end width 352 is narrow enough such that the distal end of the device 200 falls into the safety slot 306 and is received within the safety slot 306. Furthermore, the top portion 354 of the distal end does not protrude past the top surface 309 of the tray 300. This indicates that the balloons are not sufficiently inflated for use and that the device 200 has not been properly primed.

Embodiments of the present disclosure include a method of priming the device 200. Referring to FIGS. 8-13, the method includes providing the device 200 according to any of the disclosed embodiments (or equivalents thereof) enclosed in the tray 300. The device 200 is enclosed in the tray 300 such that the device 200 is positioned in the housing slot 302 such that the balloon activation lever 216 is in the extended position. The priming syringe 40 is positioned in the priming syringe slot 308.

The device 200 is then removed from the housing slot 302 and the balloon activation lever 216 is depressed into an intermediate position such that the device 200 can be positioned in the priming slot 304. The balloon activation lever 216 is only depressed sufficiently to place the device 200 into the priming slot 304 and is not fully depressed. The priming syringe 40 is then removed from the priming syringe slot 308 and filled with a volume of a fluid (e.g., sterile saline). In one embodiment, the volume of fluid is 20 milliliters (ml). The priming syringe 40 is then placed into lateral groove 324, and attached to the fill port of the device 200.

In order to prime the device 200, the plunger of the priming syringe 40 is depressed a first time to deliver a priming volume of the fluid through the fill port and into the balloons to fill the balloons with the fluid. In one embodiment, the priming volume of fluid is between about 1 ml and 2 ml. The plunger is then drawn back to create a vacuum and thereby deflate the balloons. In certain embodiments, after the plunger is drawn back, the vacuum can be held for a first time interval. In an exemplary embodiment, the first time interval is between about 1 second and about 10 seconds (e.g., 5 seconds).

After the plunger is drawn back to create a vacuum, the plunger is then depressed a second time to refill the balloon with a priming volume of the fluid. In one embodiment, the priming volume of fluid is between about 1 ml and 2 ml. The plunger is then again drawn back to create a vacuum and thereby deflate the balloons a second time. In certain embodiments, after the plunger is drawn back, the vacuum can be held for a second time interval. In an exemplary embodiment, the second time interval is between about 1 second and about 10 seconds (e.g., 5 seconds).

After the plunger is drawn back to create a vacuum for a second time, the plunger is then depressed a third time to refill the balloons with the second volume of the fluid. In one embodiment, the second volume of fluid is between about 1 ml and 2 ml. In certain embodiments, the plunger may or not be drawn back and/or depressed again after the plunger has been depressed a third time. Additionally, in some embodiments, after the plunger is depressed a third time, the plunger may be held in its position for a third time interval. In an exemplary embodiment, the third time interval can be between about 1 second and about 5 seconds (e.g., 2 seconds). The plunger is then released after being held during the third time interval and the pressure within the balloons subsequently equalizes with the pressure within the priming syringe 40.

After the plunger is depressed a third time and the pressure in the balloons is equalized, the plunger is not drawn back and the priming syringe 40 is disconnected from the fill port of the device 200. The device 200 is then be removed from the priming slot 304, thereby permitting the balloon activation lever 216 to automatically un-depress and move to the extended position as a result of its spring-biasing.

After removal of the device 200 from the priming slot 304, the balloon activation lever 216 can be depressed to activate (inflate) the balloons. When the balloons are in an activated state, the cutting blade of device 200 becomes active and can be tested by gently moving the slide button on the handle of the device to expose the cutting knife from its distal recessed position. The slide button is used to cycle the cutting blade a minimum of one time from its distal to proximal recessed positions to ensure functionality.

With the balloon activation lever 216 remaining depressed and the balloons activated, a safety test can now be performed to determine whether the tissue cutting device 200 has been properly primed. The distal end of the tissue cutting device 200 is positioned near the safety slot 306. The axial depth indicator 202 can be optionally rotated so as to be non-parallel (e.g., perpendicular) to the balloon activation lever 216. Advantageously, this step permits the axial depth indicator 202 from interfering with the safety test, for instance, by abutting any surface and thereby inadvertently causing small axial extensions of the distal end of the device 200. The distal end of the device can then be gently placed in the safety slot 306. In some embodiments, pressure should not be applied on the distal end of the device 200 so as to force the distal end into the safety slot; the distal end 104 should simply be positioned over the safety slot 306.

When the device 200 is properly primed, the balloons are inflated such that the distal end of the device 200 has a first distal end width 350. When the device 200 is properly primed, the first distal end width 350 is larger than the safety slot width 346 such that the distal end of the device 200 does not fall into in the safety slot 306 and instead rests on top of the safety slot 306. It may also be visually apparent to the operator that the balloons are properly inflated. Furthermore, a top portion 354 of the distal end should extend above the top surface 309 of the tray 300. This indicates that the balloons are sufficiently inflated for use and thus that the device has been properly primed. If the balloons are not properly primed and are underinflated such that the distal end of the device 200 falls into the safety slot 306 and is received within the safety slot 306, the device 200 should be primed again and the safety test should be performed again until the device 200 passes the test.

Once the device 200 has been primed and has passed the safety test, the device 200 can be used to perform a procedure, such as cutting a transverse carpal ligament to treat carpal tunnel syndrome. In order to prepare the device 200 for such a procedure, the balloon activation lever 216 is released into an extended position such that the balloons are deflated. The device 200 can then be placed within the carpal tunnel of the patient, and its placement with respect to different anatomical features (e.g., median nerve, ulnar vessels, superficial palmar arterial arch, palmar digital nerves, and the transverse carpal ligament, etc.) can be verified. The balloons 234a, 234b are then inflated by depressing the balloon activation lever 216, which simultaneously unlocks the cutting blade. The balloons are then locked in the inflated position used the spring-biased button 296.

The cutting blade is then be deployed by using the slider button 270. For instance, the blade can be slid in a direction from the distal end of the device 200 toward the proximal end. Accordingly, the cutting blade would engage and cut a distal transverse carpal ligament from the distal end to the proximal end of device 200. After cutting, the slider button 270 is slid distally so as to place the blade in its distal resting position. The spring-biased button 296 is then released and the balloons are deflated by releasing the balloon activation lever 116 to the extended position. The device 200 is then removed from the patient and post-surgical care (e.g., wound closure, applying bandages, etc.) is administered.

While different embodiments of a tray for a soft tissue cutting device are described, skilled artisans will understand that any of the features of one embodiment can be incorporated into the other embodiments. Any combination of the features described in any of the embodiments can be included in the tray for a soft tissue cutting device and are within the scope of the invention.

The invention claimed is:

1. A method of using a soft tissue cutting device, the method comprising:
   positioning the soft tissue cutting device in a priming slot of a tray configured for holding the soft tissue cutting device;
   attaching a priming syringe to the soft tissue cutting device;
   priming a balloon on a distal end of the soft tissue cutting device by equalizing a first pressure inside the balloon with a second pressure inside the priming syringe;
   removing the soft tissue cutting device from the priming slot; and
   positioning the distal end of the soft tissue cutting device on a safety slot included in the tray to determine whether the tissue cutting device has been properly primed.

2. The method of claim 1, wherein priming the balloon further comprises:
   depressing a plunger of the priming syringe a first time to fill the balloon with a fluid; and
   drawing back the plunger a first time to create a vacuum and deflate the balloon.

3. The method of claim 2, wherein priming the balloon further comprises:
   depressing the plunger of the priming syringe a second time to refill the balloon with the fluid;
   drawing the plunger back a second time to create a vacuum and thereby deflate the balloon;
   allowing the pressure within the balloon to equalize with the pressure in the priming syringe.

4. The method of claim 1, further comprising moving a balloon activation lever on a handle of the soft tissue cutting device from an intermediate position to an extended position the tissue cutting device is removed from the priming slot.

5. The method of claim 4, further comprising:
   inserting the soft tissue cutting device into a soft tissue of a subject;
   moving the balloon activation lever from the extended position to a depressed position; and
   deploying a blade of the soft tissue cutting device to cut the soft tissue.

6. The method of claim 5, wherein moving the balloon activation lever to the depressed position causes the balloon to expand outwardly from a shaft of the soft tissue cutting device.

7. The method of claim 5, wherein deploying the blade working end to cut the soft tissue comprises moving a slider to cause the blade to protrude out of a shaft of the soft tissue cutting device.

8. The method of claim 7, wherein the soft tissue device comprises a safety feature that prevents the slider from being moved until the balloon has expanded.

9. The method of claim 5, further comprising:
   releasing the balloon activation lever from the depressed position to deflate the balloon; and
   removing the soft tissue cutting device from the subject.

10. The method of claim 4, wherein moving the balloon activation lever from the intermediate position to the extended position causes the balloon to deflate.

11. The method of claim 4, further comprising depressing the balloon activation lever to a depressed position to inflate the balloon after removing the tissue cutting device from the priming slot and prior to positioning the tissue cutting device on the safety slot to determine whether the tissue cutting device has been properly primed.

12. The method of claim 1, wherein the safety slot has a safety slot width configured to be narrower than a distal end width of the distal end of the soft tissue cutting device when the soft tissue cutting device is properly primed for use.

13. The method of claim 1, wherein when the distal end of the soft tissue cutting device does not fall through the safety slot, the soft tissue device is properly primed.

14. The method of claim 1, wherein attaching the priming syringe to the soft tissue cutting device comprises positioning the priming syringe in a priming syringe slot in the tray.

* * * * *